(12) United States Patent
Wooster et al.

(10) Patent No.: US 12,186,216 B1
(45) Date of Patent: Jan. 7, 2025

(54) ENDOVASCULAR TOTAL AORTIC ARCH GRAFT AND METHOD OF PLACEMENT

(71) Applicant: MUSC Foundation for Research Development, Charleston, SC (US)

(72) Inventors: Mathew Wooster, Charleston, SC (US); Sanford Zeigler, Charleston, SC (US); Adam Tanious, Charleston, SC (US); Ryan Gedney, Mt. Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 18/498,104

(22) Filed: Oct. 31, 2023

Related U.S. Application Data

(60) Provisional application No. 63/520,208, filed on Aug. 17, 2023.

(51) Int. Cl.
| | |
|---|---|
| A61F 2/954 | (2013.01) |
| A61F 2/07 | (2013.01) |
| A61F 2/966 | (2013.01) |
| A61F 2/06 | (2013.01) |
| A61F 2/958 | (2013.01) |

(52) U.S. Cl.
CPC ............ *A61F 2/954* (2013.01); *A61F 2/07* (2013.01); *A61F 2/966* (2013.01); *A61F 2002/061* (2013.01); *A61F 2002/067* (2013.01); *A61F 2002/9583* (2013.01)

(58) Field of Classification Search
CPC ...... A61F 2/954; A61F 2/07; A61F 2002/061; A61F 2002/067
See application file for complete search history.

(56) References Cited

U.S. PATENT DOCUMENTS

| | | | | |
|---|---|---|---|---|
| 6,645,242 B1 * | 11/2003 | Quinn | ........................ | A61F 2/07 |
| | | | | 623/1.13 |
| 9,314,328 B2 * | 4/2016 | Dake | ......................... | A61F 2/07 |
| 9,370,437 B2 * | 6/2016 | Chuter | .................... | A61F 2/915 |
| 11,096,775 B2 | 8/2021 | Perkins | | |
| 11,534,285 B2 | 12/2022 | Perkins | | |

FOREIGN PATENT DOCUMENTS

| | | |
|---|---|---|
| EP | 2967830 B1 | 11/2017 |
| WO | 2022178378 A1 | 8/2022 |
| WO | 2022216374 A2 | 10/2022 |

* cited by examiner

*Primary Examiner* — William H Matthews
(74) *Attorney, Agent, or Firm* — Riverside Law LLP

(57) ABSTRACT

A stent graft system includes a primary body having a proximal end, a distal end, a first tubular graft material and multiple stents attached to the first tubular graft material. A first branch has a second tubular graft material forming a first branch lumen. The first branch traverses a first fenestration configured in the primary body with a first wire loaded therethrough. A second branch has a third tubular graft material and a second branch lumen. The second branch traverses a second fenestration configured in the primary body with a second wire loaded therethrough. A third branch has a fourth tubular graft material and a third branch lumen. The third branch traverses a third fenestration configured in the primary body with a third wire loaded therethrough. A method for placing a stent graft system is also described.

30 Claims, 11 Drawing Sheets

ENDOVASCULAR TOTAL AORTIC ARCH GRAFT AND METHOD OF PLACEMENT

CROSS-REFERENCE TO RELATED APPLICATIONS

This application claims priority to U.S. provisional application No. 63/520,208, filed Aug. 17, 2023, incorporated herein by reference in its entirety.

BACKGROUND OF THE INVENTION

Aortic interventions involving the aortic arch present unique challenges. Traditionally, pathology in the arch has been treated with open surgery. In patients that are unfit for open surgery, there are a lack of devices that offer the surgeon the ability to treat the patient from a completely endovascular approach. Current options and devices treat a portion of the aorta endovascularly, but still require open surgery to fully complete the repair. Some of the challenges with endovascular surgery in the aortic arch include risk of stroke with wire and device manipulation, complex anatomical branching, variable anatomy from patient to patient, lack of suitable landing zones between branching vessels, and significant movement due to the heart beating that makes landing the graft challenging, to name a few. Devices that have been proposed have various drawbacks. Several require a specific orientation for access to branching vessels, which can add precious time, increasing the chances of harming the patient and increase failure rates. Further, current devices are deployed across the target vessels such that any maldeployment or improper orientation leads to cerebral or upper extremity ischemic time. Increased manipulation in the arch is required to ensure accurate deployment.

Accordingly, there is a need in the art for an endovascular aortic graft and method of placement that offers surgeons the ability to treat wide-ranging aortic arch pathology from a completely endovascular approach while avoiding the problems described above. Embodiments described herein fit this need.

SUMMARY OF THE INVENTION

In one embodiment, a stent graft system includes a primary body having a proximal end, a distal end, a first tubular graft material and a first plurality of stents attached to the first tubular graft material; a first branch having a second tubular graft material forming a first branch lumen, wherein the first branch traverses a first fenestration configured in the primary body with a first wire loaded therethrough; a second branch having a third tubular graft material and a second branch lumen, wherein the second branch traverses a second fenestration configured in the primary body with a second wire loaded therethrough; and a third branch having a fourth tubular graft material and a third branch lumen, wherein the third branch traverses a third fenestration configured in the primary body with a third wire loaded therethrough.

In one embodiment, the first wire traverses a distal opening of the primary body, a distal opening of the first branch, a proximal opening of the first branch, and a proximal opening of the primary body. In one embodiment, a portion of the first wire wraps around an edge of the proximal opening of the primary body. In one embodiment, the second wire traverses a distal opening of the primary body, a distal opening of the second branch, a proximal opening of the second branch, and a proximal opening of the primary body. In one embodiment, a portion of the second wire wraps around an edge of the proximal opening of the primary body. In one embodiment, the third wire traverses a distal opening of the primary body, a distal opening of the third branch, a proximal opening of the third branch, and a proximal opening of the primary body. In one embodiment, a portion of the third wire wraps around an edge of the proximal opening of the primary body. In one embodiment, the first branch has a second plurality of stents attached thereto. In one embodiment, the second plurality of stents are attached to the second tubular graft material only distal of the first fenestration. In one embodiment, the second branch has a third plurality of stents attached thereto. In one embodiment, the third plurality of stents are attached to the third tubular graft material only distal of the second fenestration. In one embodiment, the third branch has a fourth plurality of stents attached thereto. In one embodiment, the fourth plurality of stents are attached to the fourth tubular graft material only distal of the third fenestration. In one embodiment, the first, second, third and fourth graft materials are a woven fabric. In one embodiment, the first branch, second branch and third branch are arranged in parallel along an exterior surface of the primary body. In one embodiment, the first branch, second branch and third branch are arranged in parallel along an interior surface of the primary body. In one embodiment, a bare stent structure configured proximal of a proximal opening of the primary body. In one embodiment, a release mechanism attached to a proximal tip of the bare stent structure. In one embodiment, a trigger wire is attached to the release mechanism. In one embodiment, a kit includes the system; an introducer sheath; and a delivery wire.

In one embodiment, a method for placing a stent graft system within a vessel includes the steps of loading the stent graft system into an elongate sheath and over a delivery wire; advancing the elongate sheath to a first site within a vessel; unsheathing a proximal portion of the stent graft system; advancing a first catheter over the first wire and through the first branch; withdrawing the first wire; advancing a first replacement wire through the first catheter; catheterizing a first branch vessel over the first replacement wire; advancing a second catheter over the second wire and through the second branch; withdrawing the second wire; advancing a second replacement wire through the second catheter; catheterizing a second branch vessel over the second replacement wire; advancing a third catheter over the third wire and through the third branch; withdrawing the third wire; advancing a third replacement wire through the third catheter; and catheterizing a third branch vessel over the third replacement wire. In one embodiment, the first target is the proximal descending thoracic aorta just distal to the left subclavian artery. In one embodiment, the step of unsheathing includes unsheathing a proximal portion of the stent graft system proximal edge of the graft is landed just distal to the left subclavian artery. In one embodiment, the method includes advancing a compliant balloon over the delivery wire to advance the elongate sheath. In one embodiment, the first replacement wire has a larger diameter than the first wire. In one embodiment, the first branch vessel is the left subclavian artery. In one embodiment, the second branch vessel is the left common carotid. In one embodiment, the second branch vessel is the innominate arteries. In one embodiment, the method includes advancing a fifth catheter over the delivery wire and through the primary body; and catheterizing the vessel over the delivery wire.

In one embodiment, a stent graft system includes a primary body having a proximal end, a distal end, a first tubular graft material and a first plurality of stents attached to the first tubular graft material; a first branch having a second tubular graft material forming a first branch lumen, wherein the first branch traverses a first fenestration configured in the primary body with a first wire loaded therethrough; and a second branch having a third tubular graft material and a second branch lumen, wherein the second branch traverses a second fenestration configured in the primary body with a second wire loaded therethrough. In one embodiment, the system includes a third branch having a fourth tubular graft material and a third branch lumen, wherein the third branch traverses a third fenestration configured in the primary body with a third wire loaded therethrough.

A method for placing a stent graft system within a vessel includes the steps of loading the stent graft system into an elongate sheath and over a delivery wire; advancing the elongate sheath to a first site within a vessel; unsheathing a proximal portion of the stent graft system; advancing a first catheter over the first wire and through the first branch; withdrawing the first wire; advancing a first replacement wire through the first catheter; catheterizing a first branch vessel over the first replacement wire; advancing a second catheter over the second wire and through the second branch; withdrawing the second wire; advancing a second replacement wire through the second catheter; catheterizing a second branch vessel over the second replacement wire.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

Figure 1A:
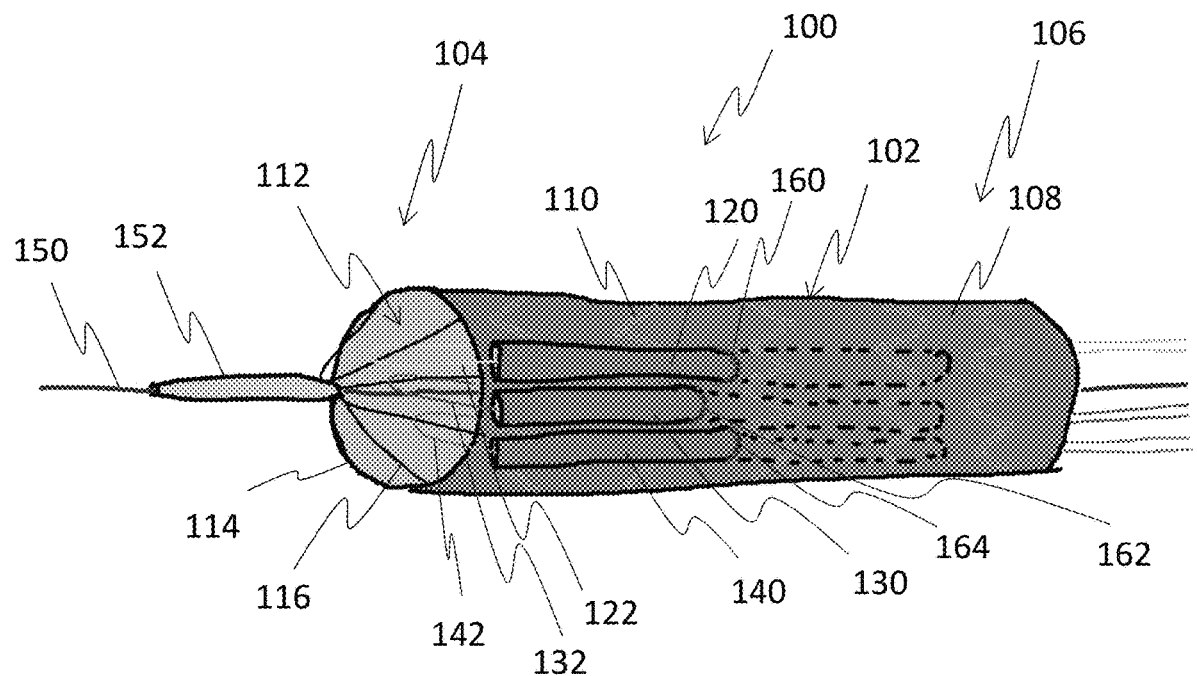
FIG. 1A is a side view and FIG. 1B is an end view of a stent graft system according to one embodiment.

It is to be understood that the figures and descriptions of the present invention have been simplified to illustrate elements that are relevant for a clearer comprehension of the present invention, while eliminating, for the purpose of clarity, many other elements found in stent graft systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is a stent graft system and method.

Embodiments of the stent graft system provide several unique advantages over other systems in the art. The embodiments described herein are not dependent on a particular orientation during insertion. Unlike other devices currently used in which maldeployment leads to inability to use the device to cannulate the branches, orientation for this design only changes the approach but does not represent an absolute failure point. Further, after deployment there is no coverage of the great vessels and therefore no cerebral or upper extremity ischemic time. All current devices are deployed across the target vessels such that any maldeployment or improper orientation leads to ischemic time and increased manipulation in the arch is required to ensure accurate deployment. Still further, this positioning ensures that procedure can be aborted at any time without losing opportunity for fixing the patient in the future. After each great vessel has been stented, the procedure can still be aborted at any time without fear of cerebral malperfusion. This deployment positioning allows embodiments of the device to be manufactured to fit any aortic anatomy allowing it to be used in emergent procedures. Branches can all be extended with balloon expandable stents or TBE limbs to allow only one size internal/external branch and the only size which would need to be variable is multiple diameters of the main thoracic stent graft.

Figure 1B:
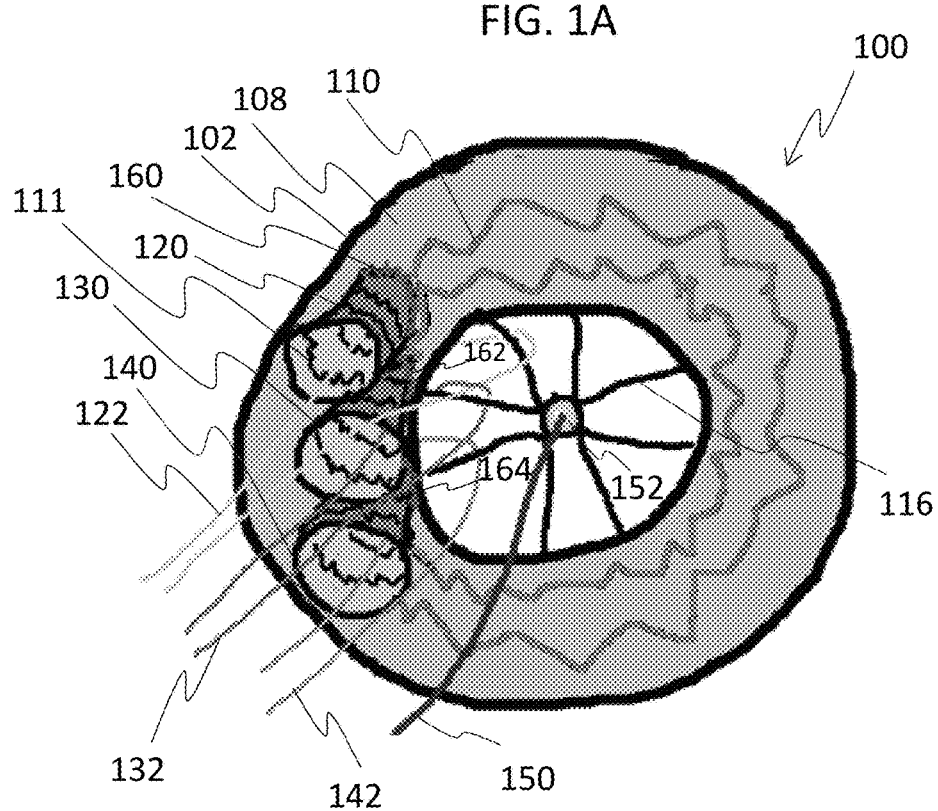

Referring now to FIGS. 1A and 1B, a stent graft system 100 is described according to one embodiment. The stent graft system 100 includes a primary body 102 having a proximal end 104, a distal end 106 and a first tubular graft material 108 extending therebetween. Multiple stents 110 are attached to the first tubular graft material 108. The stent in one embodiment can include a structure that adds rigidity or expansive force to a vessel, having for example an undulating or zigzag configuration. The stent material may be for example stainless steel, Nitinol, polymer, or another materials having elastic or super elastic properties, and may be coated, for example with a polymeric material. The stent may be configured on an exterior surface of the graft material, an interior of the graft material, or both. The stent may be self-expanding, balloon-expandable, or both. It may also be a monolithic structure wrapping around the body in a helical shape. The graft material can be designed to enhance, repair, or replace a portion or a function of a vessel, either alone or with additional components. The graft material may be a single material or a composite blend of materials (e.g. a woven fabric, or laminate).

A first branch 120 has a second tubular graft material forming a first branch lumen. The first branch 120 traverses a first fenestration 160 configured in the primary body 120 with a first wire 122 loaded therethrough. A second branch 130 has a third tubular graft material and a second branch lumen. The second branch 130 traverses a second fenestration 162 configured in the primary body 120 with a second wire 132 loaded therethrough. A third branch 140 has a fourth tubular graft material and a third branch lumen, wherein the third branch 140 traverses a third fenestration 164 configured in the primary body 120 with a third wire 142 loaded therethrough.

The first wire 122 traverses a distal opening of the primary body, a distal opening of the first branch, a proximal opening of the first branch, and a proximal opening of the primary body. A portion of the first wire 122 wraps around an edge 114 of the proximal opening 112 of the primary body. The second wire 132 traverses a distal opening of the primary body, a distal opening of the second branch, a proximal opening of the second branch, and a proximal opening of the primary body. A portion of the second wire 132 wraps around an edge 114 of the proximal opening 112 of the primary body. The third wire 142 traverses a distal opening of the primary body, a distal opening of the third branch, a proximal opening of the third branch, and a proximal opening of the primary body. A portion of the third wire 142 wraps around an edge of the proximal opening 112 of the primary body.

The first branch 120 has multiple stents 111 attached thereto distal of the first fenestration 160 (FIG. 1B). The second tubular graft material of the first branch 120 is free of stents proximal of the first fenestration 160 (FIG. 1A). Similarly, the second branch 130 and third branch 140 also have multiple stents attached thereto distal of the second fenestration 162 and third fenestration 163 respectively (FIG. 1B), and are free on stents proximal of their respective fenestrations.

The first branch 120, second branch 130 and third branch 140 can be arranged in parallel along an exterior surface of the primary body 102. The first branch 120, second branch 130 and third branch 140 can be arranged in parallel along an interior surface of the primary body 102.

A bare stent structure 116 is configured proximal of the proximal opening 112 of the primary body. The bare stents are biased to spring outwards in their relaxed state. A release mechanism 152 is attached to a proximal tip of the bare stent structure 116. A trigger wire can be attached to the release mechanism for triggering outward release of the bare stents.

Although this embodiment describes a device having a first, second and third branch, embodiments may for example have only two branches or only a single branch, or may otherwise have more than three branches such as four branches, five branches or six branches. Accordingly, in one embodiment, the stent graft system includes a primary body having a proximal end, a distal end, a first tubular graft material and a first plurality of stents attached to the first tubular graft material, and a first branch having a second tubular graft material forming a first branch lumen, wherein the first branch traverses a first fenestration configured in the primary body with a first wire loaded therethrough. In one embodiment, a second branch is present, having a third tubular graft material and a second branch lumen, wherein the second branch traverses a second fenestration configured in the primary body with a second wire loaded therethrough. In one embodiment, a third branch is present, having a fourth tubular graft material and a third branch lumen, wherein the third branch traverses a third fenestration configured in the primary body with a third wire loaded therethrough. Other embodiments may have for example four branches, five branches, six branches or more. In one embodiment, additional branches can be spaced apart or otherwise placed strategically around different portions of body, depending for example on the anatomy of the primary vessel and branching vessels being accessed. The various features of the system and method described herein can be incorporated into embodiments for one branch, two branches, three branches, four branches, five branches, six branches or more branches.

Figure 2A:
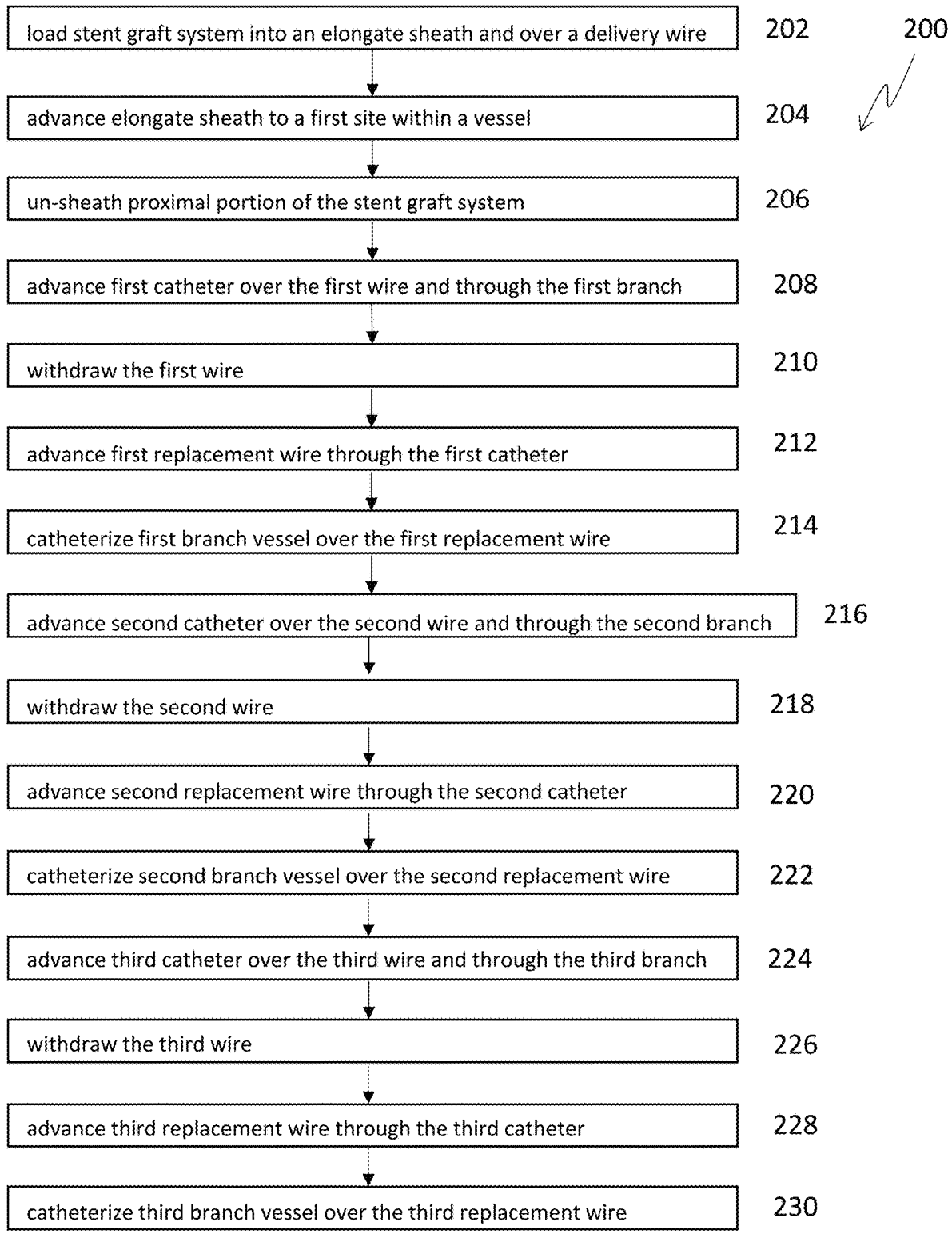
FIG. 2A is a flow chart of a method for placing a stent graft system within a vessel.
Figure 2B:
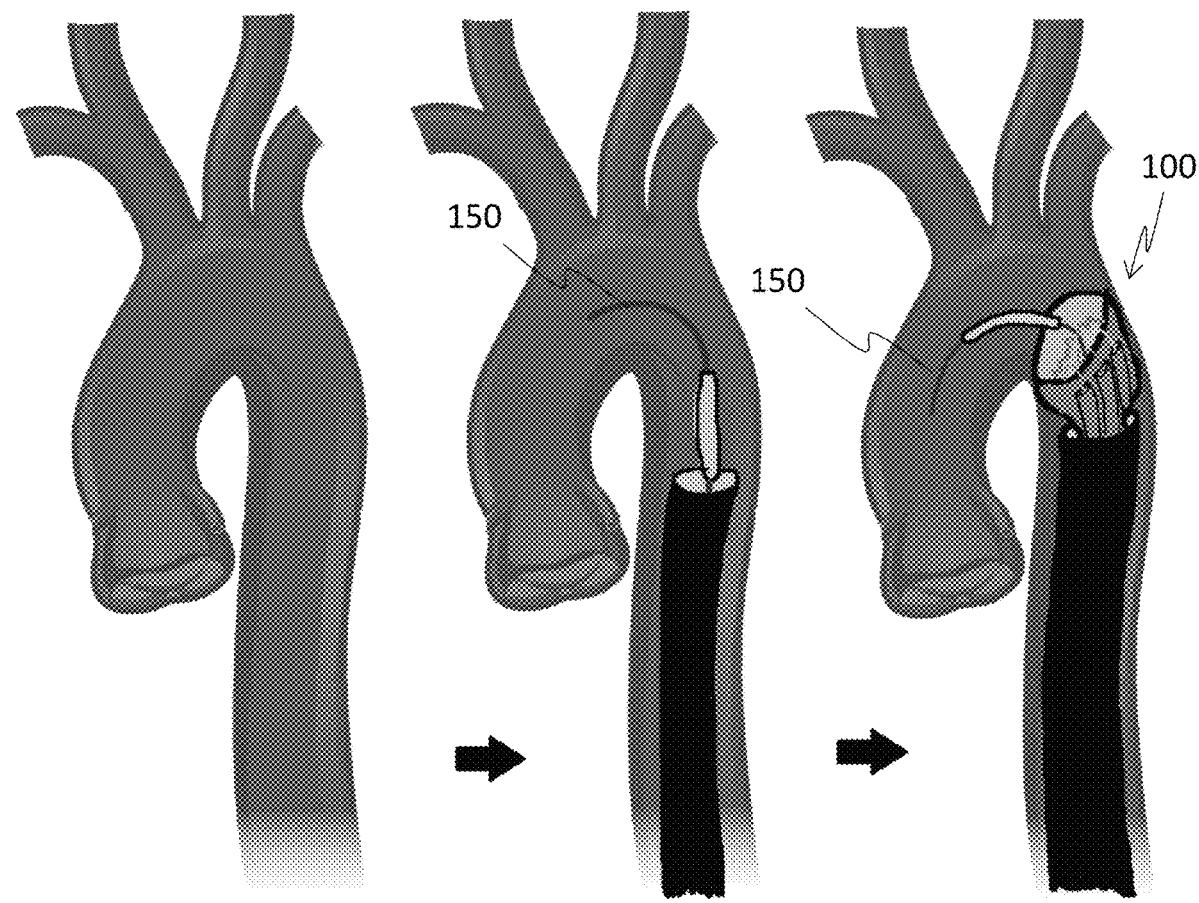
FIGS. 2B-2E are procedural diagrams according to one embodiment.
Figure 2C:
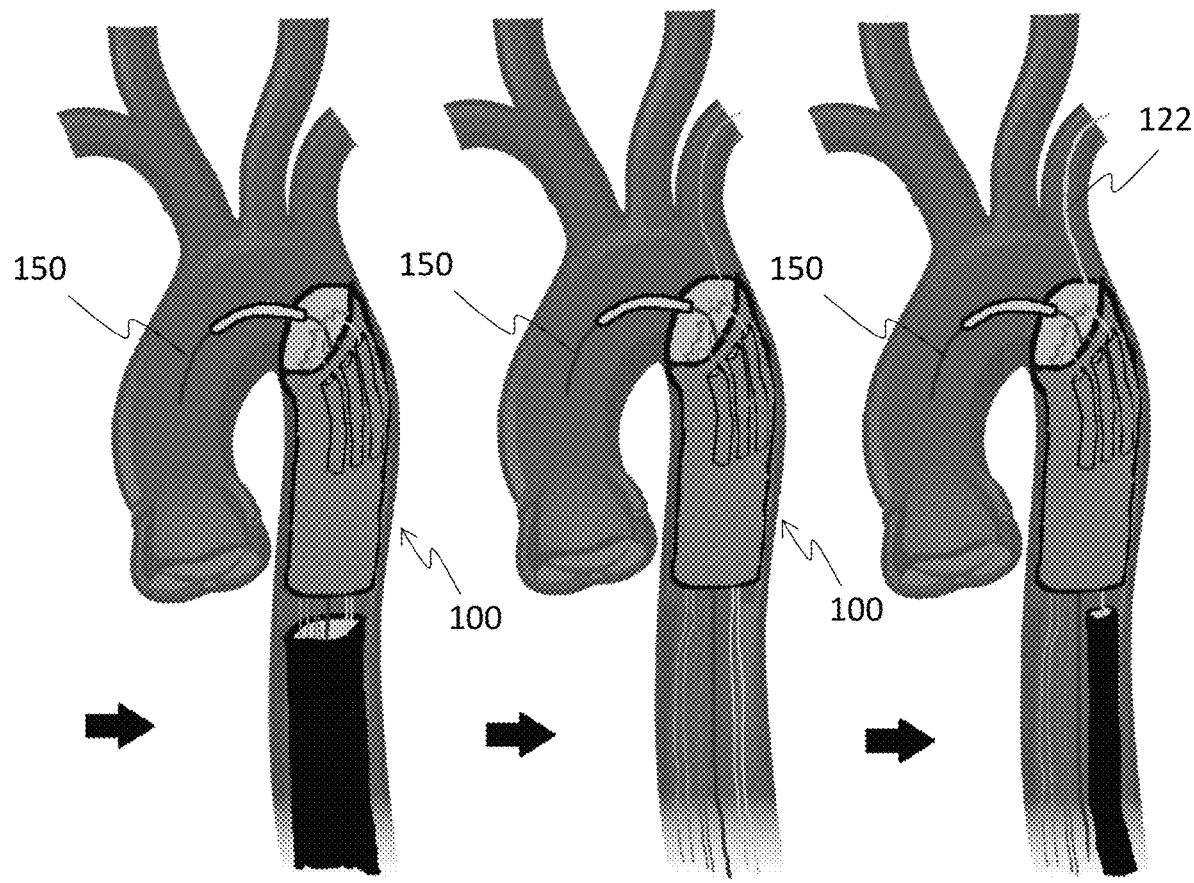
Figure 2D:
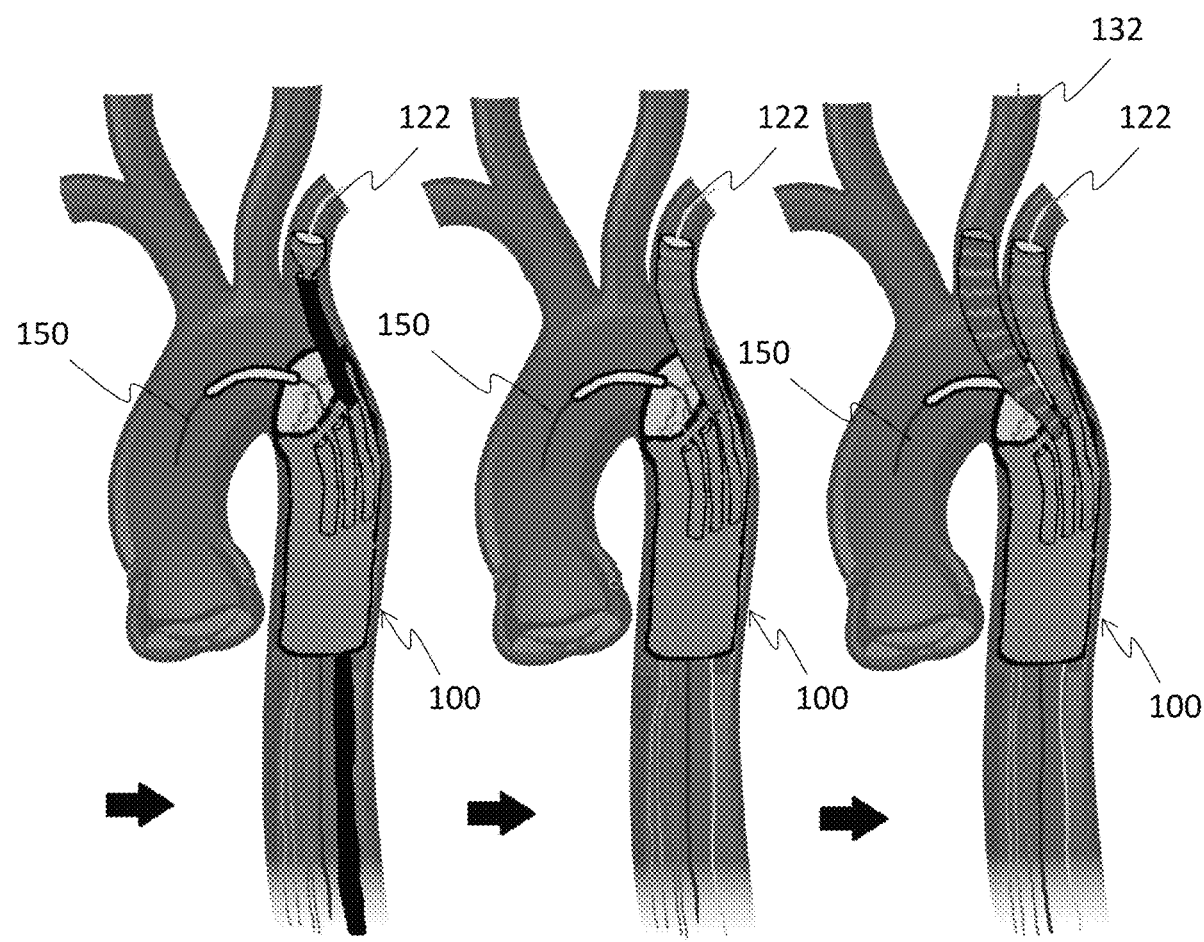
Figure 2E:
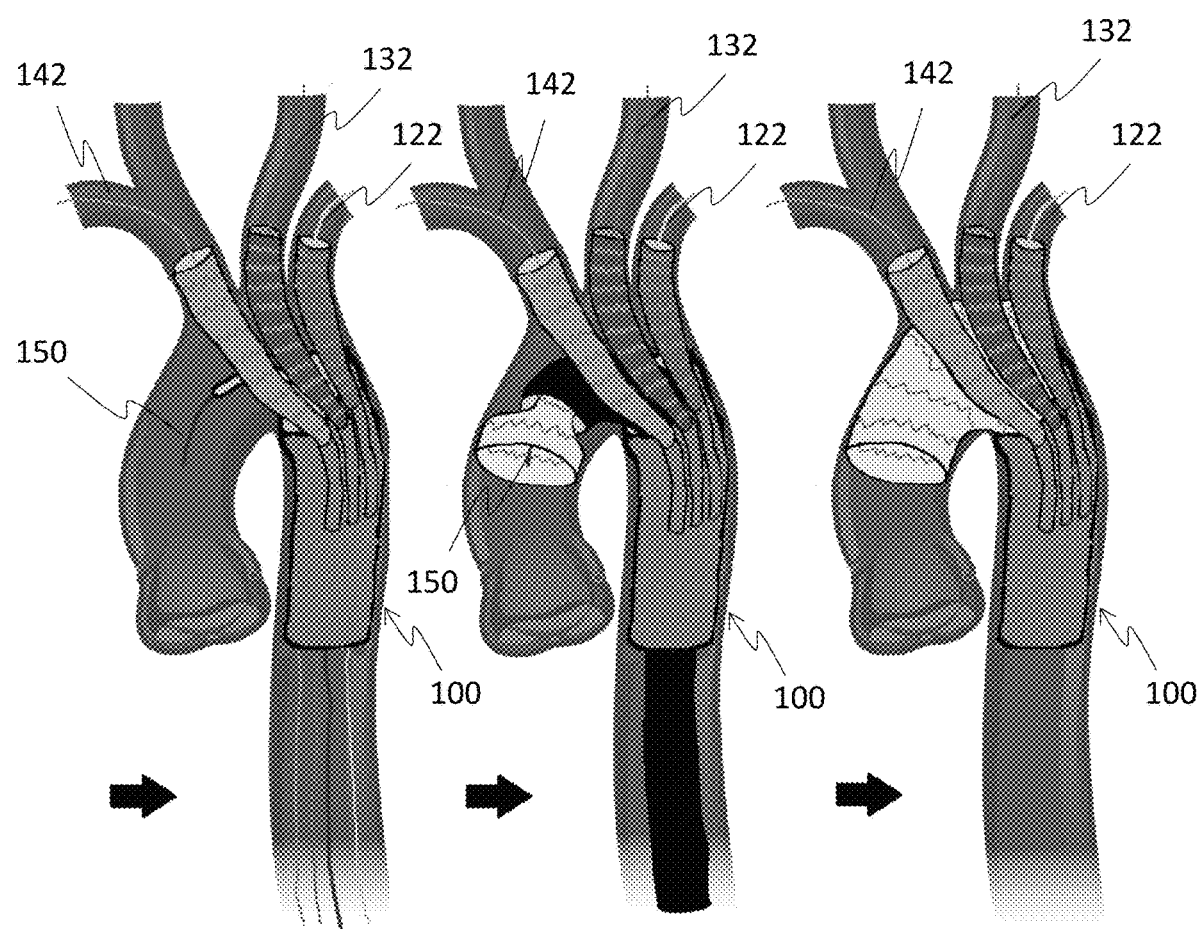

With reference now to FIG. 2A and the corresponding procedural diagrams shown in FIGS. 2B-2E, a method for placing a stent graft system within a vessel 200 is described according to one embodiment. The stent graft system is loaded into an elongate sheath and over a delivery wire 202. The elongate sheath is advanced to a first site within a vessel 204. A proximal portion of the stent graft system is unsheathed 206. A first catheter is advanced over the first wire and through the first branch 208. The first wire is withdrawn 210. A first replacement wire is advanced through the first catheter 212. A first branch vessel is catheterized over the first replacement wire 214. A second catheter is advanced over the second wire and through the second branch 216. The second wire is withdrawn 218. A second replacement wire is advanced through the second catheter 220. A second branch vessel is catheterized over the second replacement wire 222. A third catheter is advanced over the third wire and through the third branch 224. The third wire is withdrawn 226. A third replacement wire is advanced through the third catheter 228. A third branch vessel is catheterized over the third replacement wire 230. In one embodiment, the first target is the proximal descending thoracic aorta just distal to the left subclavian artery. In one embodiment, the step of unsheathing includes unsheathing a proximal portion of the stent graft system proximal edge of the graft is landed just distal to the left subclavian artery. In one embodiment, the method includes advancing a compliant balloon over the delivery wire to advance the elongate sheath. In one embodiment, the first replacement wire has a larger diameter than the first wire. In one embodiment, the first branch vessel is the left subclavian artery. In one embodiment, the second branch vessel is the left common carotid. In one embodiment, the second branch vessel is the innominate arteries. In one embodiment, the method includes advancing a fifth catheter over the delivery wire and through the primary body. In one embodiment, the method includes catheterizing the vessel over the delivery wire.

A method may also be performed in a device having a different number of branches, for example two branches or even a single branch. Accordingly, a method for placing a stent graft system within a vessel includes the steps of loading the stent graft system into an elongate sheath and over a delivery wire; advancing the elongate sheath to a first site within a vessel; unsheathing a proximal portion of the stent graft system; advancing a first catheter over the first wire and through the first branch; withdrawing the first wire; advancing a first replacement wire through the first catheter; catheterizing a first branch vessel over the first replacement wire.

The embodiments described herein have several unique features.

Location of Deployment: Distal to Left Subclavian Artery:
  (1) Negates challenges of accurate deployment with steep aortic arch angulation.
  (2) Ensures perfusion to great vessels (innominate, left carotid, left subclavian) throughout procedure.
  (3) Enables abortion of procedure at any phase without compromise of cerebral circulation or of future repair attempts.

Branch Orientation/Location:
  (1) The position of the branches is such at cannulation of the great vessels is easiest if the device is deployed with the branches between the 9:00 and 3:00 position (due anterior to due posterior rotating clockwise through 12:00 along the greater curve), but even 180 degree rotation such that the branches are opened on the lesser curve does not inhibit the cannulation of the great vessels.
  (2) Accurate deployment is one of the largest challenges in aortic arch devices.
  (3) All other currently available or disclosed devices require precise deployment of the device with a small amount of lee-way.

If mal-rotated, the graft will cover the orifice of the great vessel such that it cannot be cannulated and is ischemic If deployed to proximal or distal, the graft will cover the orifice of the great vessel such that it cannot be cannulated and is ischemic Maldeployment of any currently described device requires surgical conversion to preserve flow to the great vessels
  (4) The universality of the branch configurations allows for off-the-shelf rather than custom order design—so these devices can be ready for urgent/emergent use rather than having to be ordered weeks in advance to specific patient measurements.

Sequential Cannulation:
  (1) The distal location of the device enable sequential cannulation of each great vessel.
  (2) This means that completing the bridging stent to each vessel does not impair the ability to treat the next vessel and does not force completion of the entirety of the remaining procedure—the procedure can be aborted at any step and returned to at a later time.
  (3) Sequential cannulation ensures there is never more than one great vessel transiently occluded at any given time (during ballooning of each stent there is transient occlusion of the great vessel, since these are done in stages, we do not have to occlude all three at the same time).

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Figure 3A:
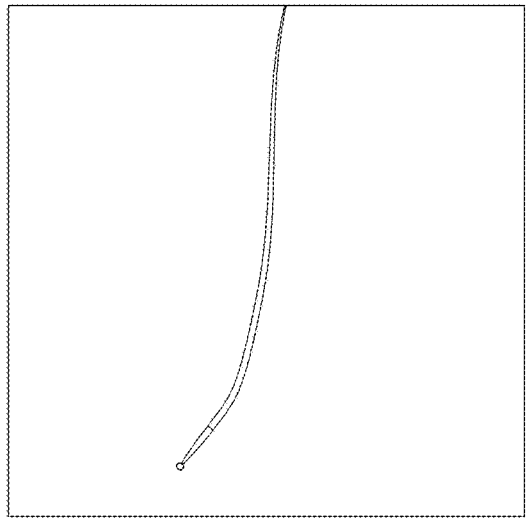
FIGS. 3A-3L are images of an experimental example of a stent graft system build according to one embodiment.
Figure 3B:
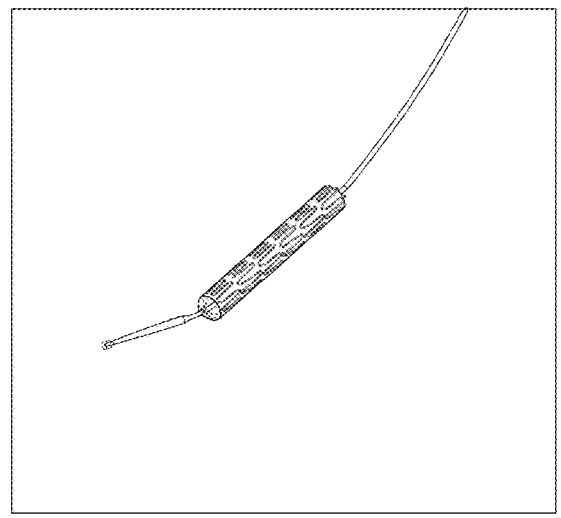
Figure 3C:
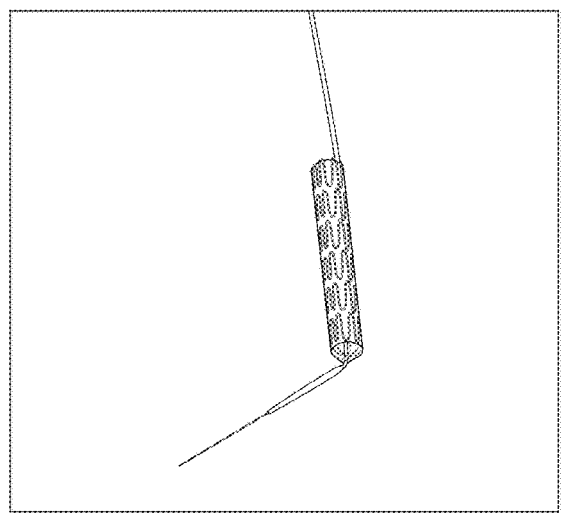

A Cook Alpha thoracic stent graft is deployed and removed from its delivery system. The pusher rod is then removed from the introducer sheath and the device reloaded onto the rod (see FIGS. 3A-3C).

Figure 3D:
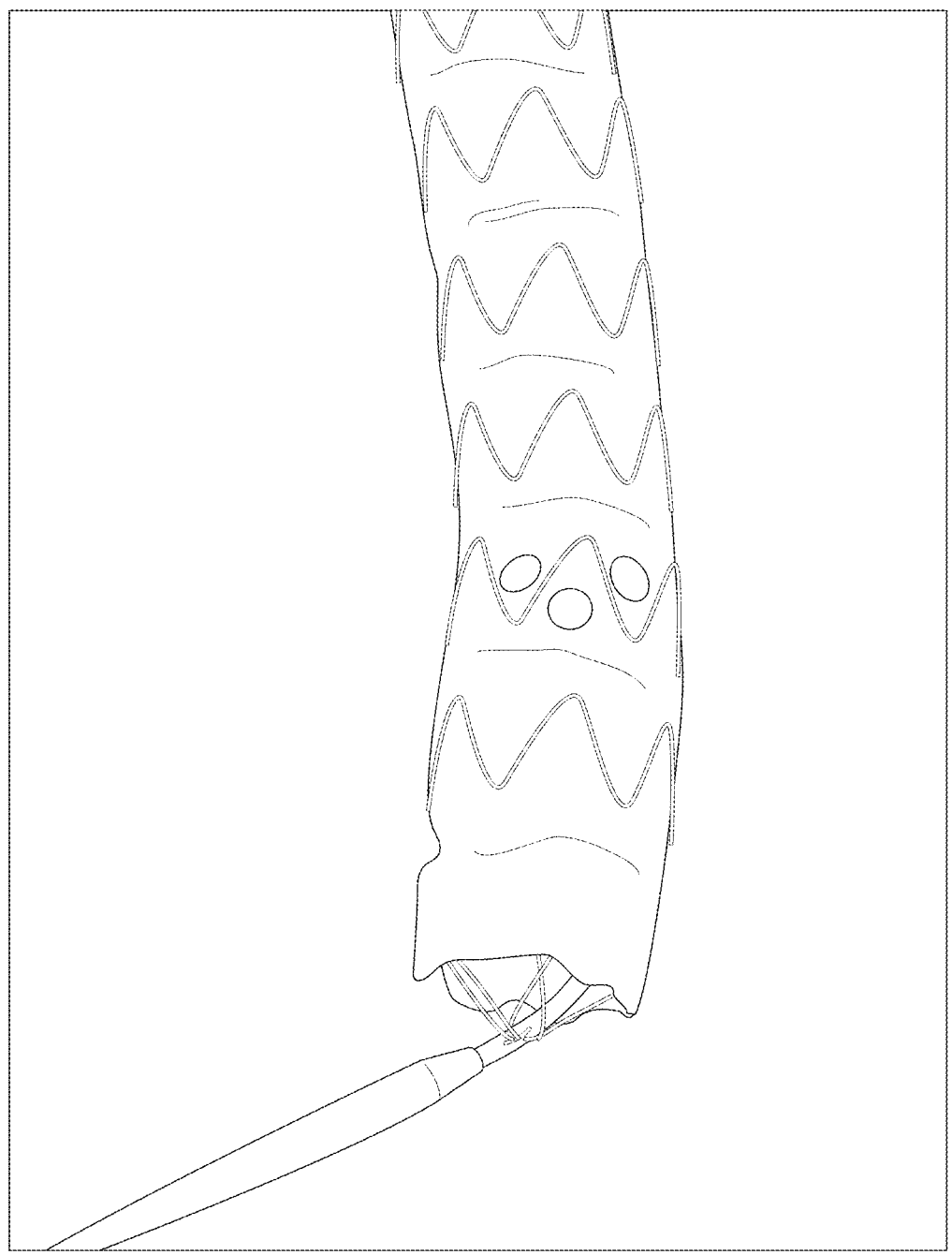
Figure 3E:
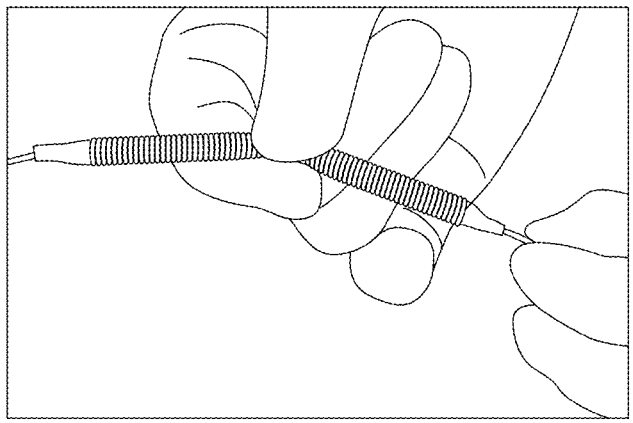
Figure 3F:
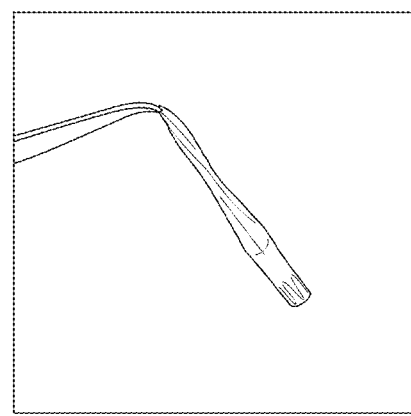
Figure 3G:
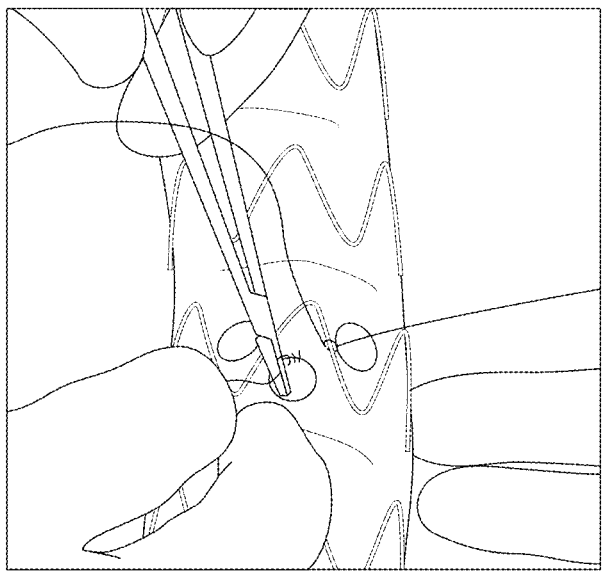
Figure 3H:
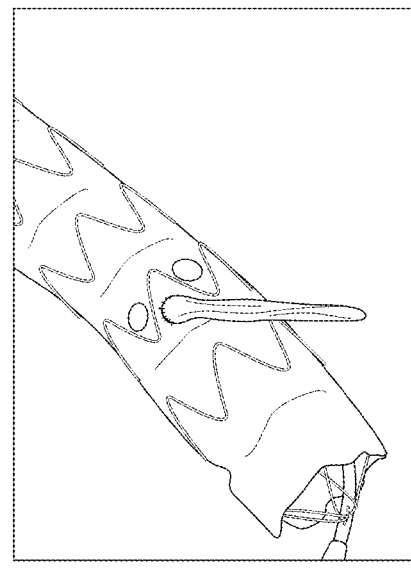
Figure 3I:
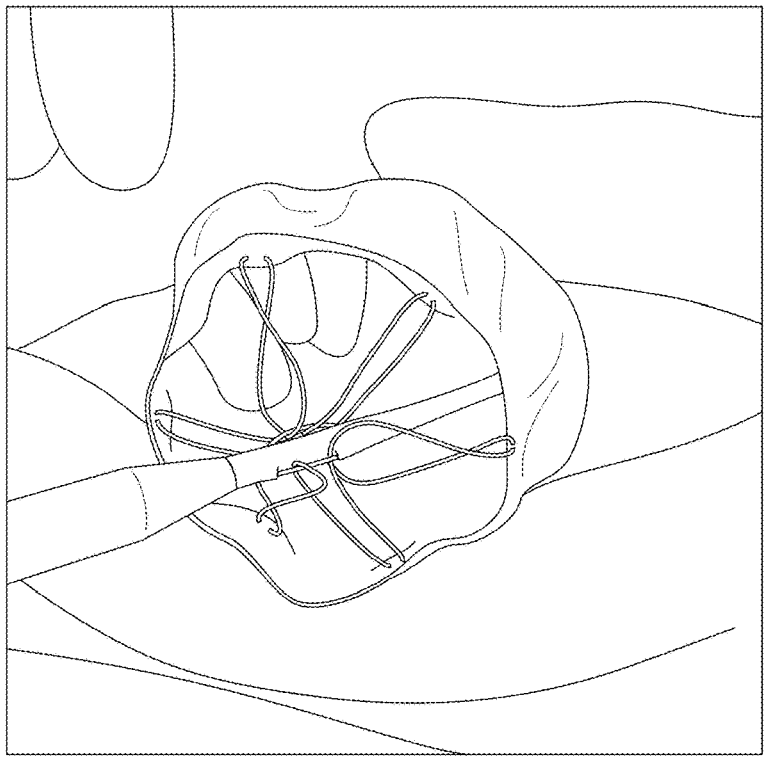
Figure 3J:
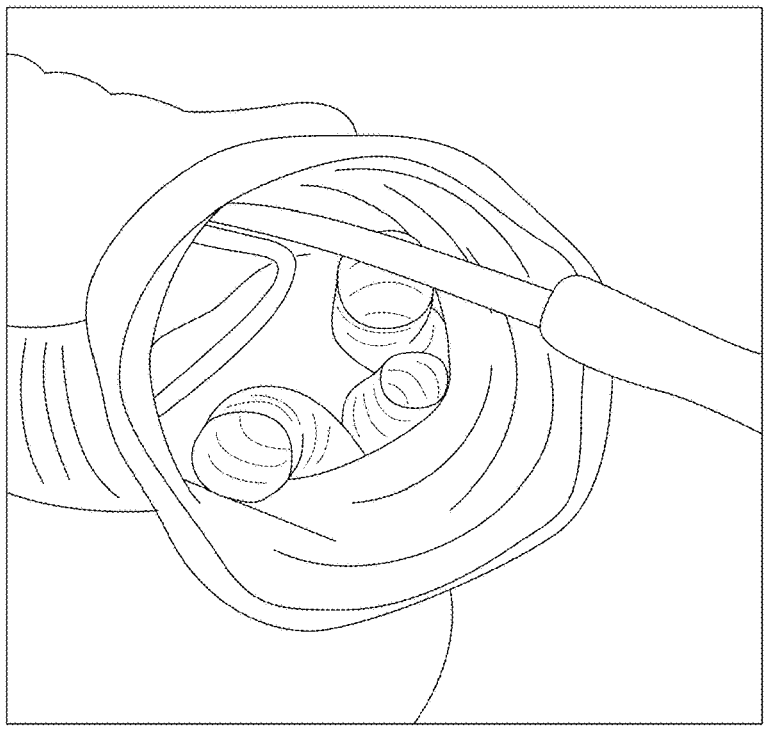
Figure 3K:
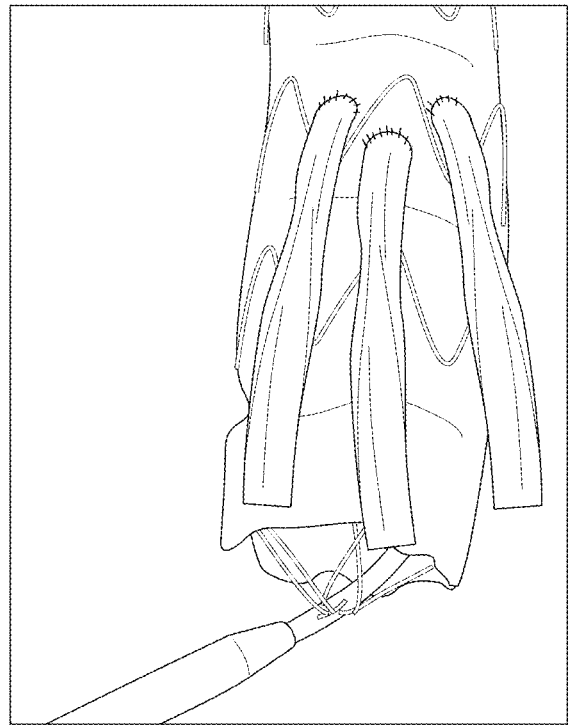
Figure 3L:
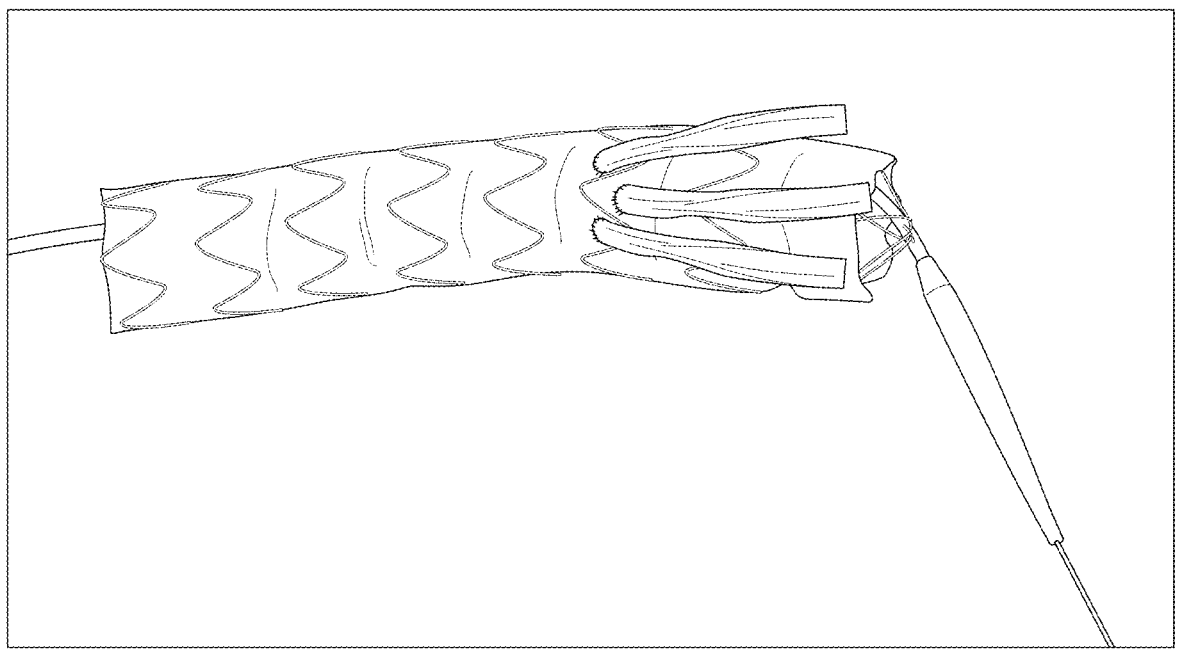

Three fenestrations are then created with the most proximal 5 cm from the proximal edge of the graft (this represents the overlap available for proximal arch extension later in the procedure) (FIG. 3D). These fenestrations are then reinforced with used of goose-neck snares sutured in place with 4-0 ethibond permanent braided suture in 360 degree running locking stitch.

Next, viabahn stent grafts of appropriate size for the intended branch vessels are de-wired and sutured on in beveled fashion with 5-0 gortex suture in standard running fashion and then tacked down to the proximal edge of the graft with 5-0 gortex horizontal mattress (FIGS. 3E-3H). 0.014 wires are then used to prewire each branch. Additionally, an 0.035 filter can be introduced into the branches as a delivery wire. Wire passes through the branching stent and then is looped back through the main body to create a rail through the branch. The device is reconstrained into peel away sheaths, sequentially reducing from 24 Fr to 22 Fr down to the lowest tolerable size. Assembled views are shown in FIGS. 3I-3L.

The patient is then prepped and draped in standard fashion and large bore arterial access obtained in bilateral femoral arteries along with right femoral venous access. Femoral venous access is used later for transvenous pacing during arch device deployment and ballooning.

An appropriately sized 65 cm Dryseal sheath is advanced to the proximal descending thoracic aorta just distal to the left subclavian artery and the device is then loaded into the dryseal sheath. The proximal edge of the graft is landed just distal to the left subclavian artery and then fully deployed by unsheathing it. At this point there is no cerebral ischemia and no bridges have been burned, the device can still be aborted at any time.

With the delivery system removed, there are now four wires extending from the dryseal sheath, the 0.035 lunderquist delivery wire and the three 0.014 branch wires.

Over the lunderquist wire a compliant balloon is advanced and used to balloon ride the sheath into the TEVAR so that it is close to the branches.

Attention is then turned to selective catheterization. A 0.035 catheter is advanced over one of the 0.014 wires and once it is through the branch the 0.014 wire is removed and a 0.035 stiff angle glidewire advanced into the aortic arch to selective catheterize the left subclavian artery then placing an amplatz super stiff 0.035 250 cm wire out the brachial artery for stable support. Next the remaining wires are used to sequentially cannulate the left common carotid and then innominate arteries leaving amplatz wire in each of these.

Covered bridging stents are then sequentially deployed and balloon catheters left in the branches but not inflated.

Contralateral femoral access is then used to cannulate the thoracic stent graft and advance a wire into the ascending aorta. Appropriately sized thoracic stent grafts are then extended from the branched graft into the ascending aorta. This is done in a modular fashion typically with an RAO oblique to land a device proximally and then an LAO oblique to land a second device distally. Proximal thoracic stent grafts are deployed under rapid venous pacing. Simultaneous ballooning is then performed by inflating the balloons into the great vessels then using compliant balloon angioplasty of the aortic stent graft under rapid pacing. This is the only cerebral ischemia time of the procedure.

Sizing of viabahns is 1-2 mm smaller than the diameter required to enable 10% oversizing into the arch branch.

Sizing of the modified device is 0-10% oversized to the aorta at the level of deployment (or of the true lumen in case of dissection). If the device will not be wall opposed at level of deployment, then a distal thoracic stent graft is deployed first and "built up" to ensure device is not mobile once deployed. Degree of oversizing of modified device is adjusted to take into account both the size of the aorta where deployed and the oversizing tolerance for overlap of devices relative to the proximal aortic graft required. i.e. if a 36 mm tevar is required in the ascending, at least a 28 mm thoracic device will be modified to ensure tolerance of the overlap.

In another experimental example, the following build procedure was completed according to the following step-by-step instructions:

Build Instructions
1. Advance/unsheath Cook Alpha Thoracic stent graft
2. Use needle or electrocautery tip to remove tip capture wires
3. Cut 4-0 prolene distal attachment tie
4. Remove delivery catheter from sheath, set sheath aside
5. Infold bare metal stent
6. Suture with 3-0 ethibond in 4 places to ensure bare metal stays infolded
7. Remount stent graft to delivery catheter
   a. Feed proximal tip capture through fabric at apex of bare metal stent×3
   b. Tie 4-0 prolene distal attachment×2
8. Mark fenestrations to be made
   a. Orient 90 degrees from precurved cannula
   b. Measure 5 cm from proximal edge of graft
   c. Adjust slightly more distal/proximal and off from 90 degrees as needed to optimize location
9. With 11 blade cut initial hole, then use heat cautery to expand size of fenestration to desired size
   a. Size determined by size of branches planned
10. Suture gooseneck snare around each fenestration using running-locking stitch with 3-0 ethibond suture
11. Deploy viabahn stents
12. Cut viabahn stents to ~10 cm long (3 cm internal+final distance from proximal edge of graft)
13. Using wire cutter to cut external metal support of viabahn ~3 cm from marker beads
    a. Remove external metal from cut point to distal edge farthest from marker beads
14. Invert viabahn
15. Anastomose viabahn to each fenestration with 5-0 goretex in standard running fashion
16. Unfold viabahn
17. Tack proximal edge of viabahn to proximal edge of thoracic graft with 5-0 gortex u stitch
18. Tack distal edge of viabahn to thoracic stent graft with 5-0 goretex by holding viabahn up to the wall of the stent graft
19. Repeat steps 12-18 for each of the remaining branches planned
20. Suture ~3 cm length of ministick wire to outer curve of stent graft (in line with precurve cannula) with 3-0 ethibond suture running locking stitch
21. Suture ~1 cm length of ministick wire to 180 degrees from 3 cm wire with 3-0 ethibond suture running locking stitch.
22. Advance 0.014 glidewire advantage through each branch with floppy end passed out the proximal end of the graft then redirected inside the thoracic graft
    a. If using different size branches, mark each wire with red rubber marker indicated which wire goes to which branch
23. Using 2-0 silk ties, double loop around each Z-stent and tighten down using hemostat, if needed add additional ties between z-stents
24. Introduce device into 24 Fr peel away sheath, then 22 Fr peel away sheath, and if needed down to 20 Fr peel away sheath, sequentially removing each double looped 2-0 silk tie as the device is advanced Procedural Steps:
1. Arterial access
   a. Bilateral femoral access with preclose technique and 8 Fr sheath introduction
   b. Selected patients: radial access, carotid access
      i. In cases of steep aortic angulation or expected difficult cannulation, radial access is pre-emptively obtained
      ii. Carotid access is only done as bail out if intraoperative difficulties
2. Venous access
   a. Bilateral femoral access with 8 Fr sheaths
3. Systemic heparinization
4. Via left femoral venous access an amplatz wire is introduced into the SVC
   a. This is a bail out wire in event of need to emergently go on cardiopulmonary bypass or ECMO
5. Via right femoral venous access transvenous pacing wires are advanced to right ventricle and tested
6. Via left femoral artery access pigtail catheter and/or intravascular ultrasound is advanced to mark left subclavian artery (landing zone)
7. Via the right femoral artery access wire is advanced to the ascending aorta and exchanged for lunderquist wire
8. If planned radial accesses were used, then 4 Fr×90 cm ansel sheaths (or 6 Fr×90 cm slender destination sheaths dependent upon patient radial artery size) are advanced into the aorta at this time
9. Right femoral arterial access is then upsized to 20-24 Fr×65 cm dryseal sheath as determined by smallest size peel away sheath the device has been constrained into
10. This sheath is advanced to the level of the left subclavian artery
11. The modified device is next advanced into the dryseal sheath
12. Orientation is confirmed using the fenestration markers and the ministick wires sutured on
    a. Orientation to the greater curve is acceptable but makes the advancement of proximal bridging stents more difficult. Orientation to the lesser curve is the most difficult and is to be avoided if at all possible, but not at risk of extensive arch manipulation. Orientation anteriorly or posteriorly is preferred—in LAO view fenestrations appear nearly head on, 3 cm ministick wire appears to outer curve, and 1 cm ministick wire appears to lesser curve
    b. Orientation does not truly matter. Unlike other devices currently used in which maldeployment leads to inability to use the device to cannulate the branches, orientation for this design only make the case easier or harder but does not represent an absolute failure point
13. Device is advance such that the proximal edge of the graft is 0-1 cm distal to the left subclavian artery and the sheath is retracted, deploying the stent graft
   a. After deployment there is NO coverage of the great vessels and therefore no ischemic time. All current devices are deployed across the target vessels such that any misdeployment or improper orientation leads to ischemic time and increased manipulation in the arch is required to ensure accurate deployment.
   b. This positioning ensures that procedure can be aborted at ANY time without burning a bridge for fixing the patient in the future.
   c. This deployment positioning allows this to be manufactured as a pre-made off the shelf device which can fit any aortic anatomy allowing it to be used in emergent procedures. Branches can all be extended with balloon expandable stents or TBE limbs to allow only one size internal/external branch and the only size which would need to be variable is multiple diameters of the main thoracic stent graft
14. The deployment cannula is retracted until the nosecone is mated with the dryseal, then the dryseal sheath is readvanced to just distal to the viabahn branches after which the delivery catheter is removed.
15. Over the left subclavian wire a nest 90 cm 4 Fr catheter/135 cm 2.6 Fr catheter is advanced until it has passed the proximal edge of the graft
16. The 0.014 wire and 2.6 Fr catheter are removed and a 260 cm Amplatz ST1 wire advanced 17.8 Fr×90 cm sheath is then advanced over this into the aortic arch.
18. 100 cm bern catheter is introduced with 260 cm stiff angle glidewire is used to cannulate the left subclavian artery, advancing a wire out to the level of the brachial artery and then exchanged for 260 amplatz ST1 wire
   a. if cannulation is unsuccessful after 2 minutes decision is made to use different catheter and/or steerable sheath versus snaring wire from radial access
19. Marking catheter is advanced over the wire, then angiogram is performed to mark the left vertebral artery and measure for the length of stent.
   a. If radial access was used, angiogram is performed through the radial sheath
20. Left subclavian stent(s) are deployed.
   a. If using Gore TBE limb, then an 8 mm viabahn is deployed first, then extended with TBE limb
   b. If using TBE limb, through and through access femoral-radial is preferred
21. Steps 15-20 are repeated for the left carotid wire and then for the innominate wire
   a. Left carotid is unique as sheath introduction is not preferred. If difficulty cannulating, ministick kit is utilized to introduce 0.018 glidewire advantage (300 cm) and 2.6 Fr×65 cm catheter is barebacked through the access rather than upsize to a sheath
22. After each great vessel has been stented, the procedure can still be aborted at ANY time without fear of cerebral malperfusion. The ONLY time during which malperfusion is a concern is once one bridging stent has been deployed but NOT complete branch treatment (i.e. if an 8 mm×7.5 cm viabahn, an 8×15 viabahn, and a 8-16 TBE limb are all required to treat the innominate, then stopping after deployment of just the two viabahns may have risk of maldeployment to the branch. The third stent should be deployed to secure the branch fully before aborting).
23. Once all three branches have been stented, appropriate sized balloons (1:1 to the viabahn size used)×10-15 cm are advanced into each branch
24. Via the left femoral artery access wire/catheter are re-advanced through the modified stent graft into the ascending aorta.
25. IVUS is used to confirm appropriate position of the wire
26. IVUS and/or pigtail angiogram are used to confirm proximal device landing position and to measure length of stent required
27. After exchanging for lunderquist the left femoral sheath is upsized to appropriate selection
   a. If using Gore thoracic stent graft, dryseal sheath 65 cm is used
   b. If using Cook stent graft, then it is directly advanced with its own sheath
28. Proximal stent graft is deployed with 5 cm overlap to modified graft
   a. During advancement/deployment simultaneous balloon inflation is performed in the branch vessels to reduce risk of embolization
   b. In most cases the length from ascending to modified graft is not ideal for a single stent graft so two devices are used. First the ascending piece is deployed. Then a second bridging stent graft is used to maximize overlap to modified device
   c. This deployment is performed under rapid pacing
   d. If multiple devices are used, branch balloons are deflated between each deployment to minimize ischemic time
29. Balloon molding is performed under rapid venous pacing using Trilobe balloon
   a. Simultaneous balloon inflation is performed in the branch vessels to reduce risk of embolization or crushing of these stents
30. Pressures are measured in bilateral arms and femoral access to ensure no significant gradient
   a. If gradient, repeat angioplasty performed as indicated to branch vessel
31. If concern on angiogram for carotid compression, second catheter is introduced to measure pressure gradient and repeat angioplasty performed if indicated
32. If distal extension of stent grafts are required they are performed at this time
33. If false lumen embolizations are required, they are performed at this time
34. Completion angiography is performed with pigtail catheter via left femoral access
35. If carotid access was required, the wire is re-advanced from the femoral access beyond the percutaneous access point. Carotid access is removed and manual pressure held×10 minutes followed by completion angiogram of the carotid to confirm no access site injury
36. Proglides are deployed in each femoral artery
37. TR bands are placed for any radial access sites and if bilateral radial accesses were used, a new a-line is placed proximal to the access points to allow continuous monitoring post operatively
38. Femoral venous access is removed with purse string stitch placement
   a. Depending upon patient status, one or both sheaths may be left to be removed later in recovery or ICU Sizing of viabahns is 1-2 mm smaller than the diameter required to enable 10% oversizing into the arch branch. Sizing of the modified device is 0-10% oversized to the aorta at the level of deployment (or of the true lumen in case of dissection). If the device will not be wall opposed at level of deployment, then a distal thoracic stent graft is deployed first and "built up" to ensure device is not mobile once deployed. Degree of oversizing of modified device is adjusted to take into account both the size of the aorta where deployed and the oversizing tolerance for overlap of devices relative to the proximal aortic graft required. i.e. if a 36 mm tevar is required in the ascending, at least a 28 mm thoracic device will be modified to ensure tolerance of the overlap.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A stent graft system comprising:
    a primary body having a proximal end, a distal end, an elongate central portion between the proximal end and the distal end, a first tubular graft material and a first plurality of stents attached to the first tubular graft material;
    a first branch having a second tubular graft material forming a first branch lumen having a first proximal opening, wherein the first branch traverses a first fenestration configured in the elongate central portion of the primary body with a first wire loaded therethrough;
    a second branch having a third tubular graft material and a second branch lumen having a second proximal opening, wherein the second branch traverses a second fenestration configured in the elongate central portion of the primary body with a second wire loaded therethrough; and
    a third branch having a fourth tubular graft material and a third branch lumen having a third proximal opening, wherein the third branch traverses a third fenestration configured in the elongate central portion of the primary body with a third wire loaded therethrough;
    wherein each of the first, second and third proximal openings are disposed adjacent to a proximal opening of the primary body and maintain a proximal facing orientation.
2. The system of claim 1, wherein the first wire traverses a distal opening of the primary body, a distal opening of the first branch, a proximal opening of the first branch, and a proximal opening of the primary body.
3. The system of claim 2, wherein a portion of the first wire wraps around an edge of the proximal opening of the primary body.
4. The system of claim 3, wherein the second wire traverses a distal opening of the primary body, a distal opening of the second branch, a proximal opening of the second branch, and a proximal opening of the primary body.
5. The system of claim 4, wherein a portion of the second wire wraps around an edge of the proximal opening of the primary body.
6. The system of claim 5, wherein the third wire traverses a distal opening of the primary body, a distal opening of the third branch, a proximal opening of the third branch, and a proximal opening of the primary body.
7. The system of claim 6, wherein a portion of the third wire wraps around an edge of the proximal opening of the primary body.
8. The system of claim 1, wherein the first branch has a second plurality of stents attached thereto.
9. The system of claim 8, wherein the second plurality of stents are attached to the second tubular graft material only distal of the first fenestration.
10. The system of claim 9, wherein the second branch has a third plurality of stents attached thereto.
11. The system of claim 10, wherein the third plurality of stents are attached to the third tubular graft material only distal of the second fenestration.
12. The system of claim 11, wherein the third branch has a fourth plurality of stents attached thereto.
13. The system of claim 12, wherein the fourth plurality of stents are attached to the fourth tubular graft material only distal of the third fenestration.
14. The system of claim 1, wherein the first, second, third and fourth graft materials are a woven fabric.
15. The system of claim 1, wherein the first branch, second branch and third branch are arranged in parallel along an exterior surface of the primary body.
16. The system of claim 1, wherein the first branch, second branch and third branch are arranged in parallel along an interior surface of the primary body.
17. The system of claim 1 further comprising:
    a bare stent structure configured proximal of a proximal opening of the primary body.
18. The system of claim 17 further comprising:
    a release mechanism attached to a proximal tip of the bare stent structure.
19. The system of claim 18 further comprising:
    a trigger wire attached to the release mechanism.
20. A kit comprising:
    the system of claim 1;
    an introducer sheath; and
    a delivery wire.
21. A method for placing a stent graft system within a vessel, the method comprising:
    loading the stent graft system of claim 1 into an elongate sheath and over a delivery wire;
    advancing the elongate sheath to a first site within a vessel;
    unsheathing a proximal portion of the stent graft system;
    advancing a first catheter over the first wire and through the first branch;
    withdrawing the first wire;
    advancing a first replacement wire through the first catheter;
    catheterizing a first branch vessel over the first replacement wire;
    advancing a second catheter over the second wire and through the second branch;
    withdrawing the second wire;
    advancing a second replacement wire through the second catheter;
    catheterizing a second branch vessel over the second replacement wire;
    advancing a third catheter over the third wire and through the third branch;
    withdrawing the third wire;
    advancing a third replacement wire through the third catheter; and
    catheterizing a third branch vessel over the third replacement wire.

22. The method of claim 21, wherein the first target is the proximal descending thoracic aorta just distal to the left subclavian artery.

23. The method of claim 21, wherein the step of unsheathing includes unsheathing a proximal portion of the stent graft system proximal edge of the graft is landed just distal to the left subclavian artery.

24. The method of claim 21 further comprising:
advancing a compliant balloon over the delivery wire to advance the elongate sheath.

25. The method of claim 21, wherein the first replacement wire has a larger diameter than the first wire.

26. The method of claim 21, wherein the first branch vessel is the left subclavian artery and the second branch vessel is one of the left common carotid and the innominate arteries.

27. The method of claim 21 further comprising:
advancing a fifth catheter over the delivery wire and through the primary body; and
catheterizing the vessel over the delivery wire.

28. A stent graft system comprising:
a primary body having a proximal end, a distal end, an elongate central portion between the proximal end and the distal end, a first tubular graft material and a first plurality of stents attached to the first tubular graft material;
a first branch having a second tubular graft material forming a first branch lumen having a first proximal opening, wherein the first branch traverses a first fenestration configured in the elongate central portion of the primary body with a first wire loaded therethrough; and
a second branch having a third tubular graft material and a second branch lumen having a second proximal opening, wherein the second branch traverses a second fenestration configured in the elongate central portion of the primary body with a second wire loaded therethrough;
wherein each of the first and second openings are disposed adjacent to a proximal opening of the primary body and maintain a proximal facing orientation.

29. The system of claim 28 further comprising:
a third branch having a fourth tubular graft material and a third branch lumen, wherein the third branch traverses a third fenestration configured in the primary body with a third wire loaded therethrough.

30. A method for placing a stent graft system within a vessel, the method comprising:
loading the stent graft system of claim 28 into an elongate sheath and over a delivery wire;
advancing the elongate sheath to a first site within a vessel;
unsheathing a proximal portion of the stent graft system;
advancing a first catheter over the first wire and through the first branch;
withdrawing the first wire;
advancing a first replacement wire through the first catheter;
catheterizing a first branch vessel over the first replacement wire;
advancing a second catheter over the second wire and through the second branch;
withdrawing the second wire;
advancing a second replacement wire through the second catheter;
catheterizing a second branch vessel over the second replacement wire.

* * * * *